(12) United States Patent
Maa et al.

(10) Patent No.: US 10,921,004 B1
(45) Date of Patent: Feb. 16, 2021

(54) ANTIVIRAL AIR-FILTERING LIGHTING DEVICE

(71) Applicant: Aleddra Inc., Renton, WA (US)

(72) Inventors: Chia-Yiu Maa, Bellevue, WA (US); Chun-Te Yu, Bellevue, WA (US)

(73) Assignee: Aleddra Inc., Renton, WA (US)

( * ) Notice: Subject to any disclaimer, the term of this patent is extended or adjusted under 35 U.S.C. 154(b) by 0 days.

(21) Appl. No.: 16/836,570

(22) Filed: Mar. 31, 2020

(51) Int. Cl.
| | | |
|---|---|---|
| *F24F 3/16* | (2021.01) |
| *F21V 33/00* | (2006.01) |
| *F21V 23/00* | (2015.01) |
| *F21Y 115/10* | (2016.01) |
| *F21Y 113/10* | (2016.01) |

(52) U.S. Cl.
CPC .......... *F24F 3/1603* (2013.01); *F21V 23/003* (2013.01); *F21V 33/0088* (2013.01); *F21Y 2113/10* (2016.08); *F21Y 2115/10* (2016.08); *F24F 2003/1628* (2013.01); *F24F 2003/1664* (2013.01); *F24F 2003/1667* (2013.01)

(58) Field of Classification Search
CPC ............. F24F 3/1603; F24F 2003/1628; F24F 2003/1667; F24F 2003/1664; F21V 33/0088; F21V 23/003; F21V 33/0096; F21V 33/0044; F21V 29/00; F21Y 2113/10; F21Y 2115/10; E04B 9/02; F04D 25/08; A61L 9/20; A61L 2209/12; F21W 2131/30

See application file for complete search history.

(56) References Cited

U.S. PATENT DOCUMENTS

| | | | | |
|---|---|---|---|---|
| 2006/0280660 A1* | 12/2006 | Weiss | ...................... | B01D 53/88 |
| | | | | 422/186.3 |
| 2020/0282097 A1* | 9/2020 | Baldi | ........................ | A61L 9/18 |

* cited by examiner

*Primary Examiner* — Joseph L Williams
*Assistant Examiner* — Jose M Diaz
(74) *Attorney, Agent, or Firm* — Han IP PLLC; Andy M. Han (57) ABSTRACT

A lighting device that comprises a housing, two light sources, at least one airway, an air filter in each airway, and an air circulation mechanism for each airway. The air filter is coated with an antiviral photocatalytic coating. The first light source contributes to the light output of the device, whereas the second light source activates the photocatalyst material in the antiviral photocatalytic coating on the air filter. As the air circulation mechanism forces the air through the air filter, the airborne microbials are trapped on the surface of the air filter, and subsequently killed and decomposed by the photocatalyst material in the antiviral photocatalytic coating. With different embodiments, the present disclosure transforms the regular lighting equipment to antiviral air-filtering equipment and brings wellness lighting to the daily life.

13 Claims, 8 Drawing Sheets

ANTIVIRAL AIR-FILTERING LIGHTING DEVICE

BACKGROUND

Technical Field

The present disclosure pertains to the field of lighting devices and, more specifically, proposes an antiviral air-filtering lighting device.

Description of Related Art

Photocatalysts are known to become active under ultraviolet light and kill bacteria by breaking down the cell wall of the bacteria. Soma, R., et al., in U.S. Pat. No. 6,242,752 teaches the use of a photocatalytic film made of anatase-type titanium oxide ($TiO_2$) on the lens of a lighting device such that, as the light originating from the lighting device shines through the titanium oxide film, the UV rays of the light activate the photocatalyst, causing it to break down the bacteria cell wall and resulting in the killing of the bacteria. One limitation with the lighting device by Soma, R., et al. is that it requires UV light to activate the photocatalyst $TiO_2$.

In U.S. Pat. No. 9,522,384, Liu L. et al. introduces a new nano $TiO_2$ structure where its photocatalytic effect can be activated by visible light with wavelength range in 400 to 450 nm. This new photocatalytic material removes the UV light restriction and enable the use of visible light with photocatalytic material for germicidal application. One such application was taught in U.S. Pat. No. 10,118,170, Maa et al. by applying photocatalytic coating on the lens of a lighting device such that the photocatalytic effect can be activated by the visible light original from the light source of the lighting device. When airborne microbial contacts the photocatalytic coating on the surface of the lens of the lighting device, it is killed and decomposed.

The anti-bacterial effect of the lighting device introduced by Maa et al while useful is somewhat limited because it only kills the airborne microbial making contact to the photocatalytic coating on its lens surface. Furthermore, Maa's teaching relies on other means for bringing the microbials to the lens surface. It lacks a proactive means of bringing the airborne microbials to the photocatalytic surface where the photocatalytic germicidal activity could take place. The present disclosure addresses the limitation of Maa's teaching by introducing a lighting device with a proactive air-filtering mechanism for circulating the ambient air through an air filter coated with photocatalytic material such that the airborne microbials are trapped by the air filter and subsequently killed and decomposed by the photocatalytic coating on the air filter.

SUMMARY

In one aspect, the lighting device comprises a housing, two light sources, at least one airway, one air filter in each airway, and an air circulation mechanism for the airway(s). The housing houses the two light sources, the at least one airway, and the air filter(s). The first light source may emit predominantly visible light (>400 nm) and account for 100% of the light output of the lighting device. The second light source is concealed inside the housing and has no contribution to the light output of the lighting device. The second light source is not meant for lighting purpose. Rather, it is used for activating the photocatalytic material coated on the surface of the air filter.

The lighting device has at least one airway. For each airway, it has an air inlet and an air outlet. There is one air filter in each airway. The air circulation mechanism sucks the ambient air through the air inlet, forces the air through the air filter, and releases the air through the air outlet. The air filter traps airborne microbials on its surface and has an antiviral photocatalytic coating on its surface. The second light source, which is not used for lighting purpose, is positioned adjacent to the air filter for activating the photocatalyst material in the antiviral photocatalytic coating. It is not required for the second light source to be positioned inside the airway. It is only necessary for the second light source to be adjacent to the air filter so that it can effectively activate the photocatalyst material in the antiviral photocatalytic coating on the air filter. When airborne microbials are trapped by the air filter, and the activated photocatalyst material in the antiviral photocatalytic coating would kill and decompose the trapped microbials.

In some embodiments, the air circulation mechanism is a fan positioned in the airway. However, other air circulation mechanism, such as an external HVAC system may also be used as the air circulation mechanism of the present disclosure so long it may move effectively the ambient air through the airway.

If using visible-light activate-able photocatalyst material, such as the one introduced by Liu et al, a visible light source can be used as the second light source for trigger the photocatalytic activity. Therefore, in some embodiments, the photocatalyst material in the antiviral photocatalytic coating on the air filter may be activate-able by visible light (>400 nm).

When using regular photocatalyst material in the antiviral photocatalytic coating, it is necessary to trigger the photocatalytic activity with UV light. Thus, in some embodiments, the second light source is a UL light source emitting predominantly UV light (<400 nm).

In some embodiments, the photocatalyst material in the antiviral photocatalytic coating contains one type of material, titanium oxide ($TiO_2$). It is also common to use $TiO_2$ with another metal for the metal may help $TiO_2$ absorb the energy in the visible light range. Therefore, in some embodiments, the photocatalyst material in the antiviral photocatalytic coating contains titanium oxide ($TiO_2$) as the primary photocatalyst and an active metal ingredient such as silver, gold, copper, zinc, nickel, or a combination thereof, as the secondary photocatalyst. Liu's teaching in U.S. Pat. No. 9,522,384 demonstrates the use of $TiO_2$ as the primary photocatalyst and silver as the secondary photocatalyst.

The titanium dioxide is classified as a semiconducting photocatalyst. Recently, technology breakthrough has demonstrated that noble metal nanoparticles such as gold (Au) and silver (Ag) can are a class of efficient photocatalysts working by mechanisms distinct from those of semiconducting photocatalysts (https://pubs.rsc.org/en/content/article-landing/2013/gc/c3gc40450a#!divAbstract). The present disclosure is not limited to the use of semiconducting photocatalysts such as $TiO_2$ only. The metal-based photocatalysts would work just as well. Therefore, in some embodiments, the photocatalyst material in the antiviral photocatalytic coating contains a noble metal nanoparticle such as gold (Au) or sliver (Ag) as the main photocatalyst.

In some embodiments, the first light source may comprise white light LEDs each emitting predominantly visible light (>400 nm). In some embodiments, the second light source may comprise UV LEDs each emitting predominantly UV light (<400 nm).

In some embodiments, the first light source may further comprise a third light source and a fourth light source. Both emit predominantly visible light (>400 nm), and the color temperature of the third light source is higher than the color temperature of the fourth light source. The use of the third light source with a higher color temperature is for providing a higher circadian stimulus, which is desirable for some lighting applications for mimicking the daylight. Similarly, the use of the fourth light source with a lower color is to provide a lower circadian stimulus for nighttime. Moreover, in some embodiments, the color temperature of the first light source may be tunable via a controller by mixing the combination ratio of color temperatures of the third light source and the fourth light source. This color tuning may be done manually, or it may be done automatically according to a circadian schedule stored in a memory module. The circadian schedule will transition the color temperature of the first light source from warm white (2700K) to cold white (6500K) at dawn and revert the color temperature back to warm white at sunset, thus emulating color transition of the sunlight.

In the event of using visible-light activate-able photocatalyst material in the antiviral photocatalytic coating on the air filter, the second light source may emit predominantly visible light (>400 nm). In this case, the need of concealing the second light source may be relaxed. As a result, in some embodiments, the second light source is not completely concealed inside the housing and may account for 1% to 20% of the light output of the lighting device, whereas the first light source may account for 80% to 99% of the light output of the lighting device. In some embodiments, the first and the second light sources may use same type of LED. In this case, the LEDs closest to the air filter are regarded as the second light source, and the rest LEDs as the first light source, and they both contribute to the light output of the lighting device.

BRIEF DESCRIPTION OF THE DRAWINGS

The accompanying drawings are included to aid further understanding of the present disclosure, and are incorporated in and constitute a part of the present disclosure. The drawings illustrate a select number of embodiments of the present disclosure and, together with the detailed description below, serve to explain the principles of the present disclosure. It is appreciable that the drawings are not necessarily to scale, as some components may be shown to be out of proportion to size in actual implementation in order to clearly illustrate the concept of the present disclosure.

DETAILED DESCRIPTION OF PREFERRED EMBODIMENTS

Overview

Various implementations of the present disclosure and related inventive concepts are described below. It should be acknowledged, however, that the present disclosure is not limited to any particular manner of implementation, and that the various embodiments discussed explicitly herein are primarily for purposes of illustration. For example, the various concepts discussed herein may be suitably implemented in a variety of lighting apparatuses having different form factors.

The present disclosure discloses a lighting device that comprises a housing, two light sources, at least one airway, an air filter in each airway, and an air circulation mechanism for each airway. The first light source emits visible light and accounts for 100% the light output of the lighting device. The second light source is concealed inside the housing, and it activates the photocatalyst material in the antiviral photocatalytic coating the air filter. The air circulation mechanism forces the ambient air through the air filter and the air filter traps airborne microbials. The trapped microbials are subsequently killed and decomposed by the activated photocatalyst material in the antiviral photocatalytic coating.

Example Implementations

Figure 1A:
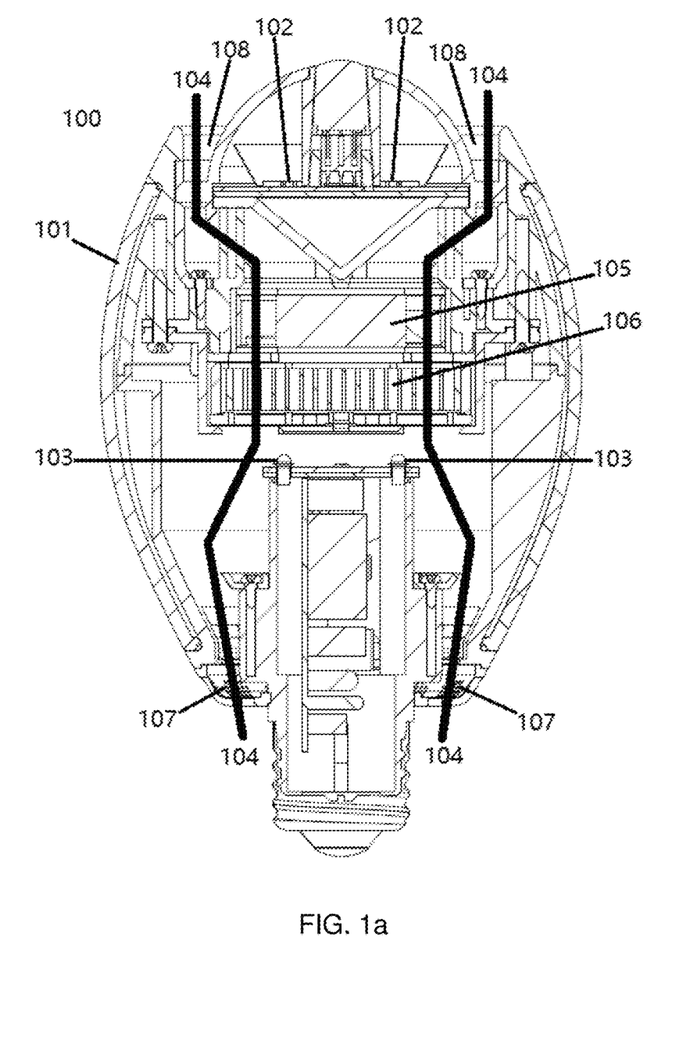
FIG. 1a schematically depicts a cross-section diagram of an LED screw-in lamp as an embodiment of the present disclosure.
Figure 1B:
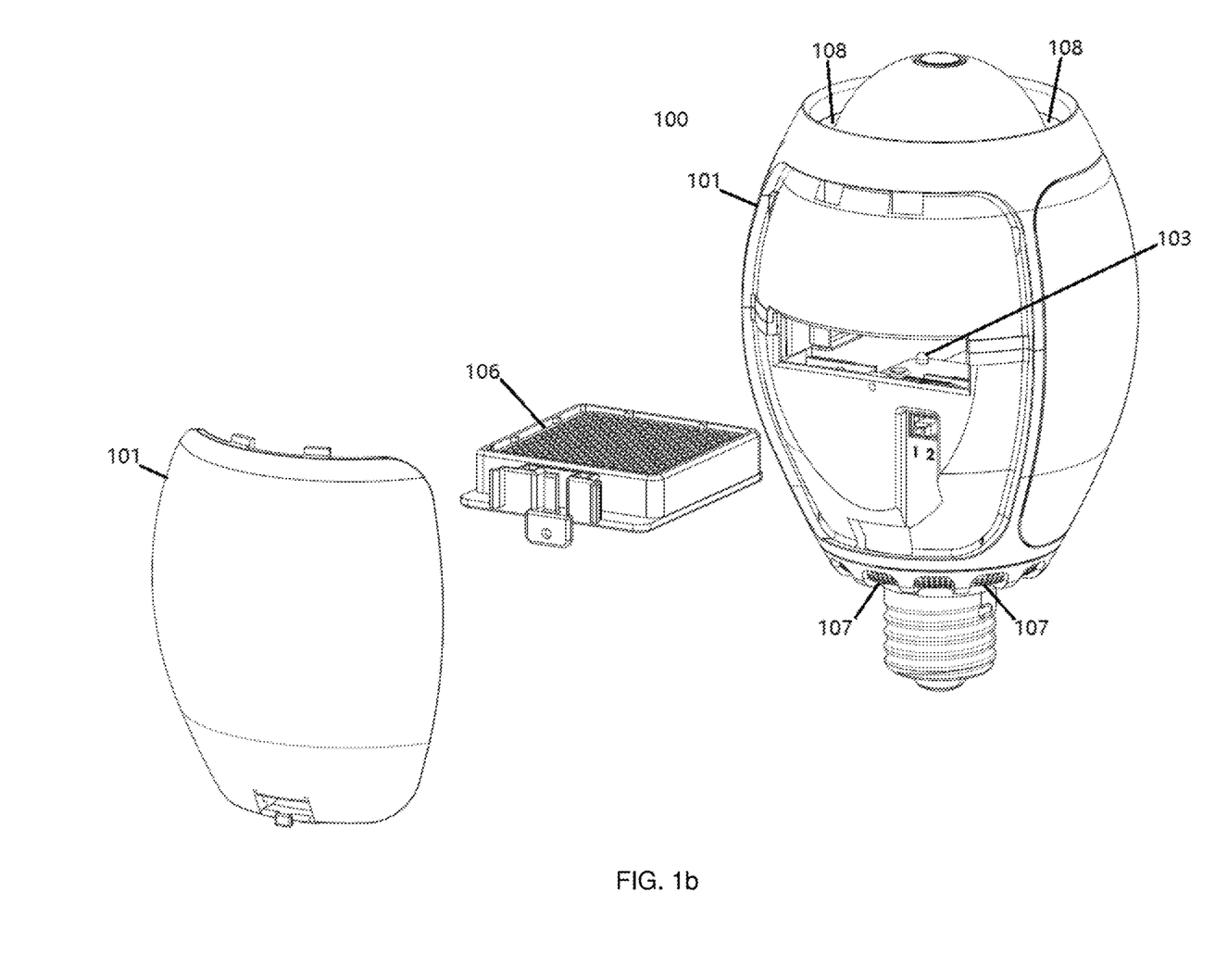
FIG. 1b schematically depicts a diagram of the screw-in lamp from another perspective.
Figure 1C:
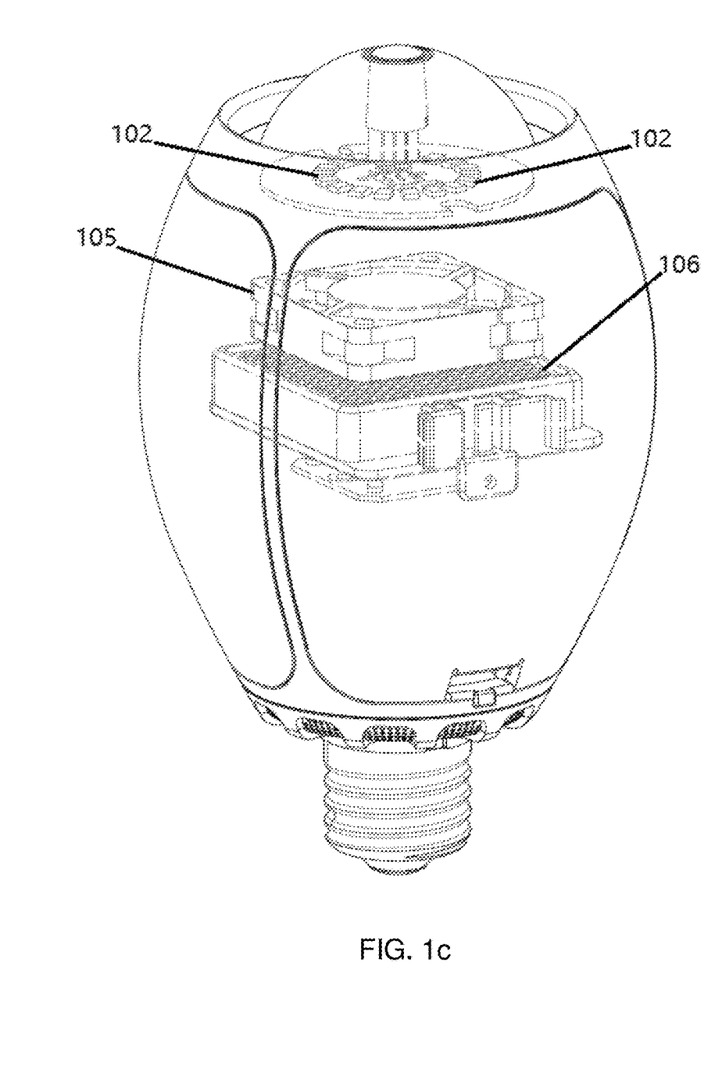
FIG. 1c schematically depicts a diagram of the screw-in lamp from yet another perspective.

FIG. 1a-1c show an embodiment of the lighting device of the present disclosure in a form of an LED screw-in lamp 100. This lamp has a housing 101, the first light source 102, the second light source 103, one airway 104, and one fan 105 and one air filter 106. The first light source 102 comprises multiple LEDs on top of the lamp emitting predominantly white light in the >400 nm wavelength range, and accounts for 100% light output of the lighting device. The second light source 103 comprises multiple UV LEDs and are concealed inside the housing and has no contribution to the light output of the lighting device. The airway 104 has an air inlet 107 and an air outlet 108. The fan 105 and the air filter 106 are positioned inside the airway 104. The fan 105 sucks the ambient air through the air inlet 107, forces the air through the air filter 106, and releases the air through the air outlet 108. The air filter 106 has antiviral photocatalytic coating 109 on its surface. The second light source 103 is positioned adjacent to the air filter 106 for activating the photocatalyst material in the antiviral photocatalytic coating 109. In this embodiment, the second light source 103 is inside the airway 104.

Figure 1D:
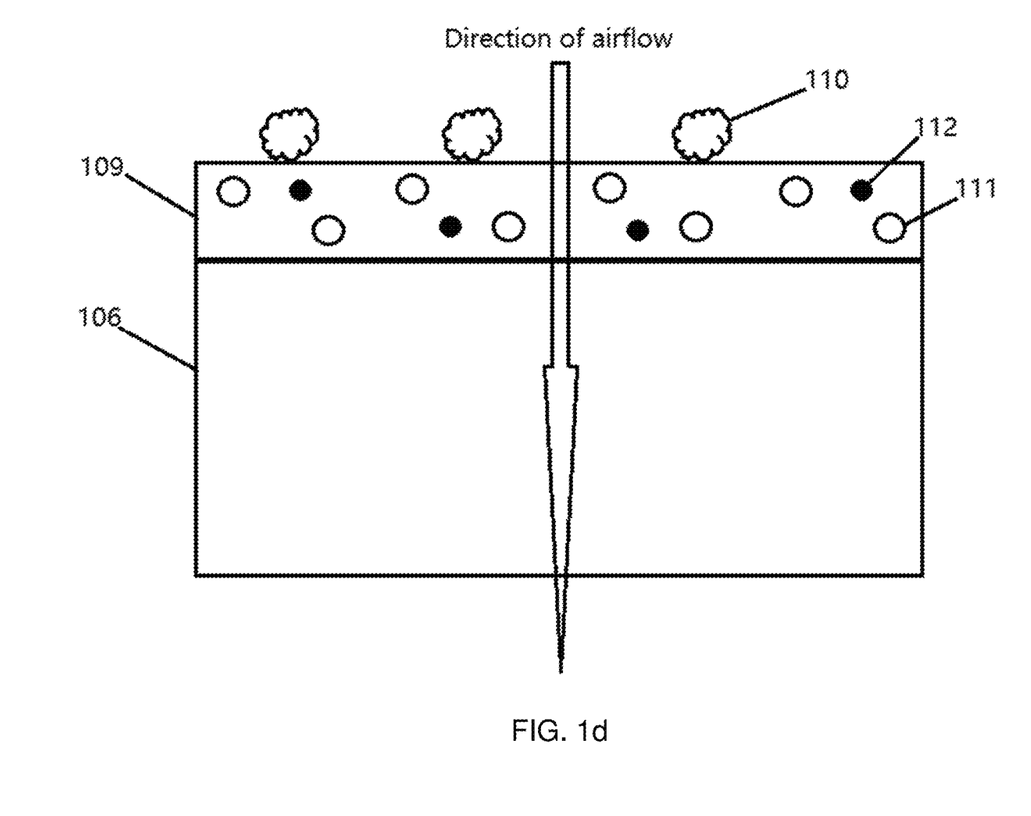
FIG. 1d schematically depicts the air filter and its antiviral photocatalytic coating of the lamp, and the trapped microbials.

In FIG. 1d, as the air passes through the air filter 106, the airborne microbials 110 are trapped on the surface of the air filter. The photocatalyst material in the antiviral photocatalytic coating 109 activated by the second light source 103 kills and decomposes the trapped microbials 110. The photocatalyst material contains nano anatase-type $TiO_2$ 111 as its primary photocatalyst and nano silver 112 as its secondary photocatalyst. When using $TiO_2$ and nano silver as photocatalyst, visible light LEDs can be used as the second light source 103 and still achieve adequate photocatalytic effect. It is also foreseeable to use metals other than nano silver as the secondary photocatalyst. Moreover, it is anticipated to use noble metal nanoparticle such as gold (Au) and silver (Ag) as the main photocatalyst in lieu of a semiconducting photocatalyst $TiO_2$.

Figure 2A:
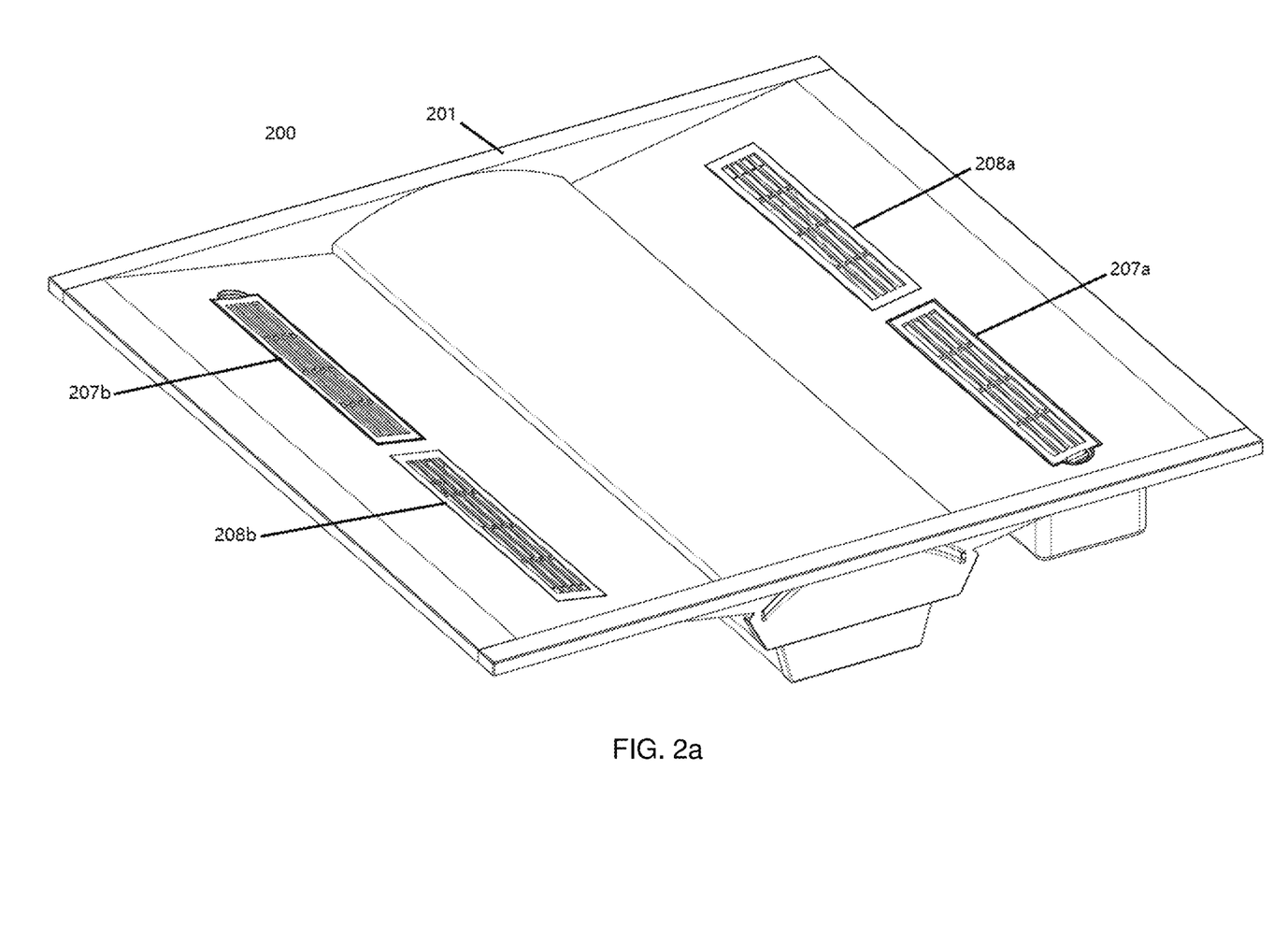
FIG. 2a schematically depicts an exterior view of an LED troffer fixture.
Figure 2B:
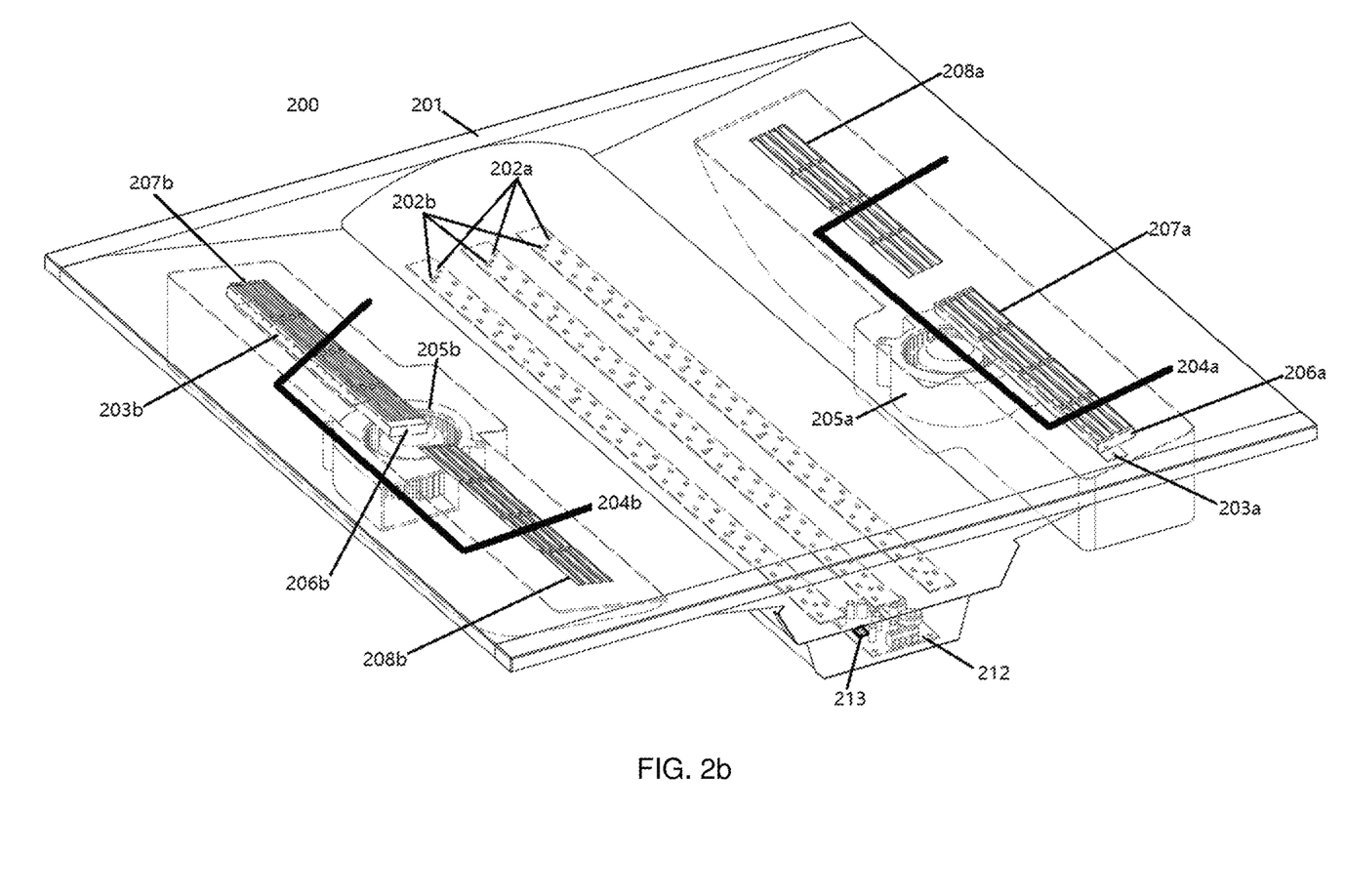
FIG. 2b schematically depicts a look-through view of the troffer.

FIGS. 2a and 2b show an embodiment of the lighting device of the present disclosure in a form of an LED troffer fixture 200. This troffer has a housing 201, the first light source 202a,202b, the second light source 203a,203b, two airways 204a,204b, two fans 205a,205b and two air filters 206a,206b. The first light source comprises six rows of LEDs on three PCBs. Out of the six rows of LEDs, three rows are 2700K LEDs 202a and the other three rows are 6500K LED 202b. The 2700K LEDs produce a lesser circadian stimulus and is more suitable for nighttime lighting, whereas the 6500K LED produce a higher circadian stimulus and is more suitable for daytime use. The combined light output of 2700K and 6500K LEDs sets the total light output of the lighting device. Since they each emits predominantly visible light in the >400 nm wavelength range, their combined light is also in the >400 nm wavelength range. A controller 212 is used to color-tune the light output of the light device by changing the mixing ratio of the light output of the 2700K LEDs 202a and the 6500K LEDs 202b. Moreover, a memory module 213 is used to store a circadian schedule. The controller 212 can thus color-tune the light output of the first light source automatically according the circadian schedule stored in the memory module 213. The circadian schedule will transition the color temperature of the first light source from warm white (2700K) to cold white (6500K) at dawn and revert the color temperature back to warm white at sunset, thus emulating color transition of the sunlight.

Figure 2C:
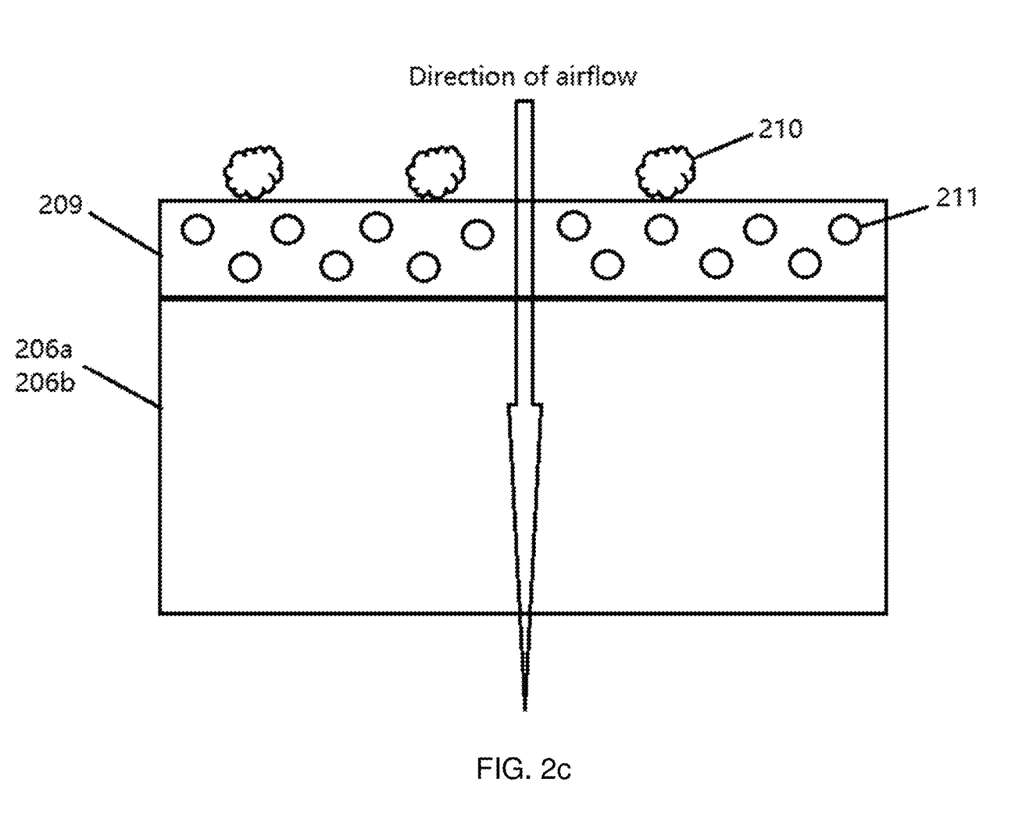
FIG. 2c schematically depicts the air filter and its antiviral photocatalytic coating of the troffer, and the trapped microbials.

The construction of the two airways 204a and 204b are the same, therefore the description below is on the airway 204a. The second light source 203a concealed in the housing comprises multiple UV LEDs and has no contribution to the light output of the lighting device. The airway 204a has an air inlet 207a and an air outlet 208a. The fan 205a and the air filter 206a are positioned inside the airway 204a. As the fan 205a forces the air through the airway 204a, the airborne microbials 210 are trapped on the surface of the air filter 206a. The surface air filter 206a is coated with an antiviral photocatalytic coating 209. As shown in FIG. 2c, the antiviral photocatalytic coating 209 contains only one type of photocatalyst material 211, $TiO_2$. When the photocatalyst material 211 is activated by the second light source 203a, it kills and decomposes the trapped microbials 210. There is only one type of photocatalyst material $TiO_2$ used in this case, because the larger number of UV LEDs 203a,203b provide adequate activation on $TiO_2$.

Figure 3:
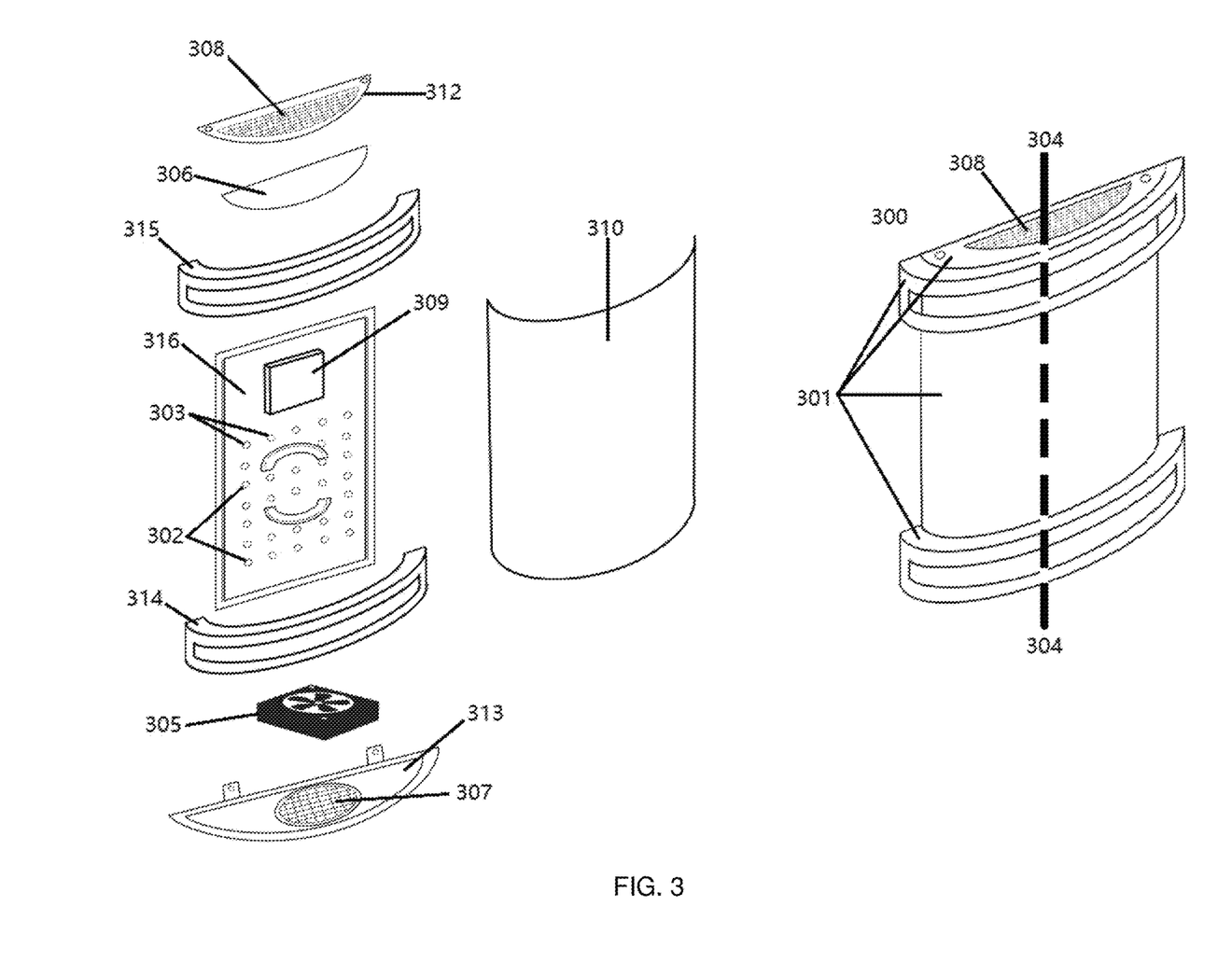
FIG. 3 schematically depicts a diagram of an LED wall sconce fixture and its cross-section.

FIG. 3 show an embodiment of the lighting device of the present disclosure in a form of an LED wall sconce fixture 300. The diagram on the right is an exterior view of the wall sconce and the diagram on the left is an exploded view of the same. The housing includes the top cover 312, the bottom cover 313, the lens 310, the back plate 316, and two decorative rims 314,315. The first light source comprises multiple LEDs, and the second light also comprises multiple LEDs adjacent to the air filter 306 which is on the top of the wall sconce. The fan 306 is positioned at the bottom of the wall sconce. Both the fan 305 and the filter 306 are inside the airway 304. The airway 304 passes through the air chamber inside the housing 301 and has an inlet 307 and an outlet 308. The LED driver 309 is mounted on the back plate 316. Though not shown in FIG. 3, the structure of the air filter is similar to the one shown in FIG. 1d, where the antiviral photocatalytic coating on the surface of the air filter comprising $TiO_2$ as the primary photocatalyst and nano silver as the secondary photocatalyst. The uniqueness of this wall sconce embodiment is in that the first light source 302 and the second light source 303 use the same type of LEDs. They only differ in their relative adjacency to the air filter 306. Moreover, the second light source also contributes to the light out of the wall sconce.

Additional and Alternative Implementation Notes

Although the techniques have been described in language specific to certain applications, it is to be understood that the appended claims are not necessarily limited to the specific features or applications described herein. Rather, the specific features and examples are disclosed as non-limiting exemplary forms of implementing such techniques.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

What is claimed is:

1. A lighting device comprises:
   a housing;
   two light sources comprising a first light source and a second light source;
   an airway;
   an air filter in the airway;
   an air circulation mechanism corresponding to the airway;
   wherein, in operation:
      the housing houses the two light sources, the at least one airway, and the air filter,
      the first light source emits predominantly visible light (>400 nm) and accounts for 100% of a light output of the lighting device,
      the second light source is concealed inside the housing and has no contribution to the light output of the lighting device,
      the at least one airway has an air inlet and an air outlet,
      the air circulation mechanism sucks an ambient air through the air inlet, forces the air through the air filter, and releases the air through the air outlet,
      the air filter traps airborne microbials on a surface thereof and has an antiviral photocatalytic coating on the surface,
      the second light source is positioned adjacent to the air filter and activates a photocatalyst material in the antiviral photocatalytic coating, and
      the airborne microbials trapped by the air filter are decomposed by the activated photocatalyst material in the antiviral photocatalytic coating.

2. A lighting device of claim 1, wherein the air circulation mechanism comprises a fan positioned in the airway.

3. A lighting device of claim 1, wherein the photocatalyst material in the antiviral photocatalytic coating on the air filter is activatable by visible light (>400 nm).

4. A lighting device of claim 1, wherein the second light source emits predominantly ultraviolet (UV) light (<400 nm).

5. A lighting device of claim 1, wherein the photocatalyst material in the antiviral photocatalytic coating on the air filter contains titanium oxide ($TiO_2$).

6. A lighting device of claim 1, wherein the photocatalyst material in the antiviral photocatalytic coating on the air filter contains titanium oxide ($TiO_2$) as a primary photocatalyst and an active metal ingredient such as silver, gold, copper, zinc, nickel, or a combination thereof, as the secondary photocatalyst.

7. A lighting device of claim 1, wherein the photocatalyst material in the antiviral photocatalytic coating on the air filter contains a noble metal nanoparticle gold (Au) or sliver (Ag) as a main photocatalyst.

8. A lighting device of claim 1, wherein the first light source comprises white-light light emitting diodes (LEDs) each emitting predominantly visible light (>400 nm).

9. A lighting device of claim 1, wherein the second light source comprises ultraviolet (UV) light emitting diodes (LEDs) each emitting predominantly UV light (<400 nm).

10. A lighting device of claim 1, wherein the first light source further comprises a third light source and a fourth light source, wherein both the third light source and the fourth light source emit predominantly visible light (>400 nm), and wherein a color temperature of the third light source is higher than a color temperature of the fourth light source.

11. A lighting device of claim 10, further comprising:
a controller,
wherein a color temperature of the first light source is tunable via the controller by mixing a combination ratio of the color temperatures of the third light source and the fourth light source, either manually or automatically according to a circadian schedule stored in a memory module of the controller.

12. A lighting device of clai—m 1, wherein the second light source is partially and not completely concealed inside the housing and accounts for 1% to 20% of the light output of the lighting device, and wherein the first light source accounts for 80% to 99% of the light output of the lighting device.

13. A lighting device of claim 12, wherein the first and the second light sources use a same type of light emitting diode (LED).

* * * * *